US012655119B2

(12) United States Patent
Lanier et al.

(10) Patent No.: US 12,655,119 B2
(45) Date of Patent: Jun. 16, 2026

(54) CRYSTALLIZATION OF CANNABINOIDS

(71) Applicant: Chemtor, LP, Lockhart, TX (US)

(72) Inventors: William Lanier, West Jordan, UT (US); Michael Peter Noll, III, Denver, CO (US); William David Winget, Denver, CO (US)

(73) Assignee: Chemtor, LP, Lockhart, TX (US)

( * ) Notice: Subject to any disclaimer, the term of this patent is extended or adjusted under 35 U.S.C. 154(b) by 562 days.

(21) Appl. No.: 18/167,974

(22) Filed: Feb. 13, 2023

(65) Prior Publication Data

US 2023/0257358 A1 Aug. 17, 2023

Related U.S. Application Data

(63) Continuation of application No. PCT/US2021/071111, filed on Aug. 5, 2021.

(60) Provisional application No. 63/089,269, filed on Oct. 8, 2020.

(51) Int. Cl.
*C07D 311/80* (2006.01)

(52) U.S. Cl.
CPC ........ *C07D 311/80* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 7,618,544 B2 | 11/2009 | Massingill, Jr. | |
| 8,128,825 B2 | 3/2012 | Massingill | |
| 9,765,000 B2 | 9/2017 | Nadal Roura | |
| 2005/0266108 A1 | 12/2005 | Flockhart et al. | |
| 2010/0034945 A1 | 2/2010 | Arango Moreno | |
| 2016/0228385 A1 | 8/2016 | Sievers et al. | |
| 2017/0008870 A1* | 1/2017 | Dibble ................ | C07D 311/80 |
| 2017/0349517 A1 | 12/2017 | Dickman et al. | |
| 2017/0349518 A1 | 12/2017 | Dickman et al. | |
| 2018/0162828 A1* | 6/2018 | Nadal Roura ..... | B01D 11/0492 |
| 2018/0273501 A1* | 9/2018 | Robertson ........... | B01D 9/0059 |
| 2020/0102283 A1* | 4/2020 | Dibble .................. | B01D 9/004 |

OTHER PUBLICATIONS

International Search Report and Written Opinion of the International Search Authority issued by the U.S. Patent and Trademark Office for International Application No. PCT/US2021/071111 dated Dec. 23, 2021. (11 pages).

* cited by examiner

*Primary Examiner* — Valerie Rodriguez-Garcia
(74) *Attorney, Agent, or Firm* — Haynes and Boone, LLP

(57) ABSTRACT

A method for crystallization of cannabinoids includes: providing a substantially pure cannabinoid isolate; dissolving the cannabinoid isolate in a crystallization solvent; removing solvent by evaporation until the solution reaches saturation; adding a seed crystal of said cannabinoid; maintaining a supersaturated solution throughout the recrystallization process by the continual evaporation of solvent throughout the crystallization process by incubating the solution under heat and/or vacuum and repeating this process until crystals of the desired size have been produced.

10 Claims, 2 Drawing Sheets

CRYSTALLIZATION OF CANNABINOIDS

CROSS-REFERENCE TO RELATED APPLICATIONS

The present application is a continuation of PCT International Application No. PCT/US2021/071111 filed Aug. 5, 2021, and entitled "CRYSTALLIZATION OF CANNABINOIDS", which claims priority to U.S. Provisional Application No. 63/089,269 filed Oct. 8, 2020, and entitled "CRYSTALLIZATION OF CANNABINOIDS," which are hereby incorporated by reference in their entirety.

TECHNICAL FIELD

The present disclosure is related to the crystallization of cannabinoids. More particularly, this disclosure is related to methods and systems for producing large, high purity crystals of cannabinoid acids and neutral cannabinoids.

BACKGROUND

Cannabinoids occur in the hemp plant, *Cannabis sativa*, primarily in the form of cannabinoid carboxylic acids (referred to herein as "cannabinoid acids"). The more abundant forms of cannabinoid acids include tetrahydrocannabinolic acid (THCA), cannabidiolic acid (CBDA), cannabigerolic acid (CBGA) and cannabichromic acid (CBCA). Other acid cannabinoids include, but are not limited to, tetrahydrocannabivaric acid (THCVA), cannabidivaric acid (CBDVA), cannabigerovaric acid (CBGVA) and cannabichromevaric acid (CBCVA). "Neutral cannabinoids" are derived by decarboxylation of their corresponding cannabinoid acids. The more abundant forms of neutral cannabinoids include tetrahydrocannabinol (THC), cannabidiol (CBD), cannabigerol (CBG) and cannabichromene (CBC). Other neutral cannabinoids include, but are not limited to, tetrahydrocannabivarin (THCV), cannabidivarin (CBDV), cannabigerovarin (CBGV), cannabichromevarin (CBCV) and cannabivarin (CBV).

There are several examples of methods to prepare crystalline extracts of various cannabinoids from the crude oil extracts of the *Cannabis sativa* plant. For instance, U.S. Patent Application Publication No. 2005/0266108 A1, the entirety of which is hereby incorporated by reference, describes methods for the production of enriched extracts of THCA, CBDA, THCV, CBG and CBC as crystalline solids. U.S. Pat. No. 9,765,000 B2, the entirety of which is hereby incorporated by reference, describes the uses of multiple rounds of recrystallization of crude extracts as a method to prepare substantially pure isolates of THC, THCA, THCV, CBD, CBDA, CBDV, CBG and CBGA. This approach beings with a crude extract and lends to crystal formation in a process that is much slower than the current embodiment described herein.

Currently, processing of *Cannabis* for products such as CBD isolate typically includes a preliminary step of decarboxylating the cannabinoid acids to form neutral cannabinoids. The heat associated with short path, wiped film and other distillation methods used to purify cannabinoids decarboxylates the acid cannabinoids to produce neutral cannabinoid isolates. The use of these methods is due to the desirability of the neutral cannabinoids in the bulk market and the difficulty of separating the cannabinoid acids from the neutral cannabinoids. As such, high purity crystal isolates of cannabinoid acids are less available on the market and, if available, are very expensive. The products which are available are small crystals, generally 95% or less in purity and often colored from pale yellow to orange-brown. Accordingly, there remains a need for an economical method of preparing high-purity crystalline isolates of cannabinoid acids and cannabinoids.

DETAILED DESCRIPTION

The following descriptions are provided to explain and illustrate embodiments of the present disclosure. The described examples and embodiments should not be construed to limit the present disclosure. The disclosure provides a technique developed to grow large cannabinoid acid (such as THCA) or cannabinoid crystals in a non-pressurized open container with the use of heat and/or vacuum.

Figure 1:
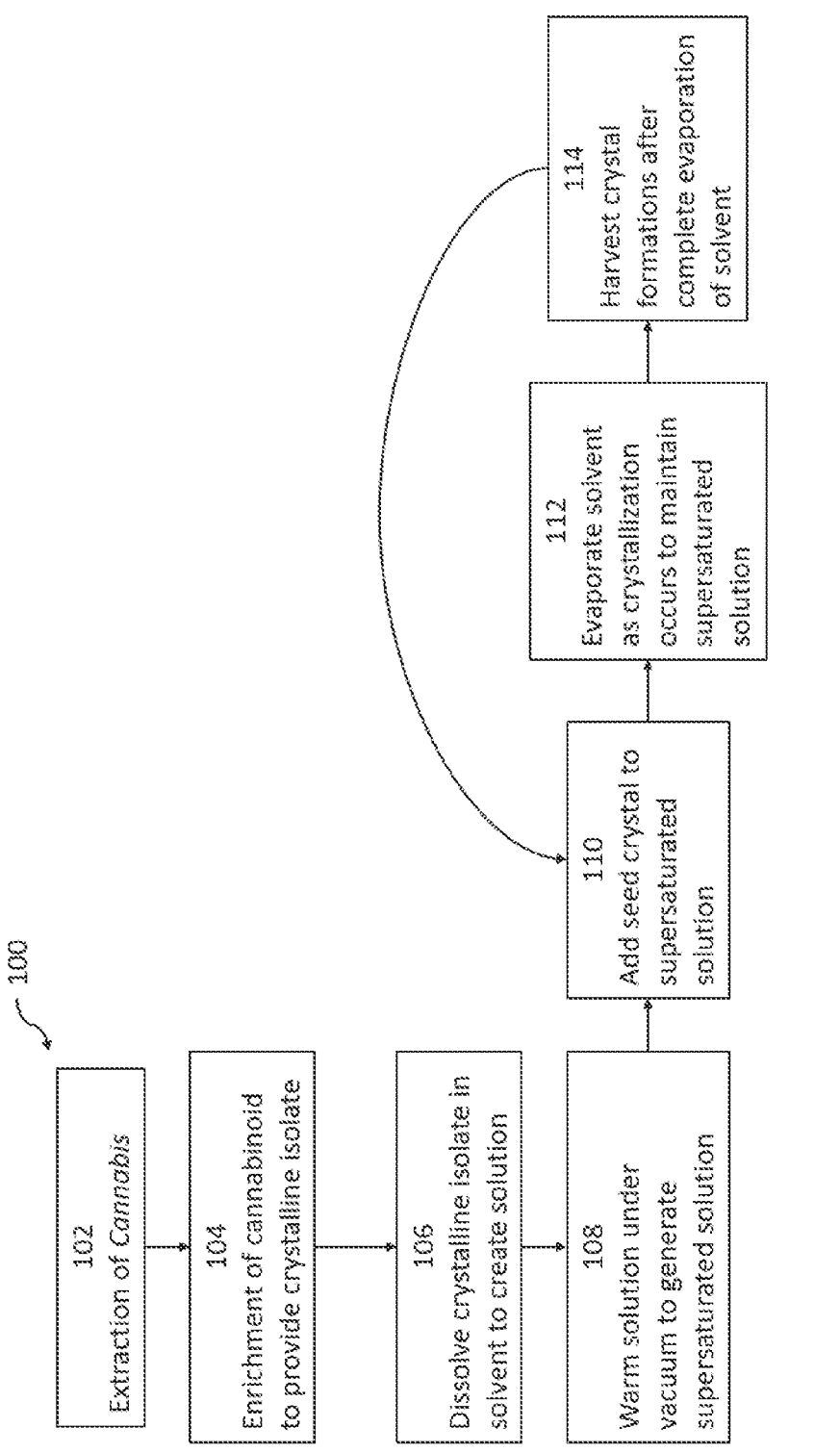
FIG. 1 is a schematic diagram of a crystallization process according to an embodiment of the present disclosure.

With reference to FIG. 1, a schematic diagram of a crystallization process 100 is shown. As an initial step 102, *cannabis* oil may be extracted from the *Cannabis sativa* plant. In one or more embodiments, the *cannabis* oil is extracted using a non-polar hydrocarbon solvent, such as propane, butane, pentane, hexane, heptane, etc. In one or more embodiments, the starting oil has a single cannabinoid acid present at a concentration of 65% or higher. While lower quality oils can be used, as well as the use of polar solvent extractions such as ethanol or $CO_2$, they may require a pretreatment, such as processing through a fiber film conduit reactor such as that described in described in U.S. Pat. Nos. 7,618,544 and 8,128,825, both of which are incorporated by reference herein in their entireties, to enrich the cannabinoid acids or cannabinoids to the desired level. Currently, commercial breeding has produced specific *Cannabis* strains that produce high levels of THCA, CBDA, CBGA, CBCA, THCVA, CBDVA or CBGVA. Any of these strains may be suitable for use in the present disclosure.

Next in a step 104, the starting material *cannabis* oil is further processed to enrich and isolate a single cannabinoid acid or cannabinoid (collectively, "cannabinoid"). In some embodiments, the *cannabis* oil may be subjected to flash chromatography to separate the desired cannabinoid from all other cannabinoids and any plant-derived impurities present in the oil. One of skill in the art will recognize that the exact mixture of solvents used for the flash chromatography will vary depending on the cannabinoid of interest, the purity of the starting material and the material used to pack the flash column. In fact, the desired separation can be achieved using a variety of chromatographic techniques in addition to flash chromatography, such as High-performance liquid chromatography (HPLC), Centrifugal Partition Chromatography (CPC), Countercurrent Chromatography (CCC), Simulated Moving Beds, etc. Some of these chromatographic separation techniques have the ability to produce high purity extracts of individual cannabinoids even when the starting material is a complex mixture of multiple cannabinoid species. In one or more embodiments, the chromatography step uses butane extracted oil rich in THCA, the solvents used are pentane and methanol, and the column packing material is uncapped silica. The chromatography peak representing the purified cannabinoid of interest is isolated from the output of the chromatography unit, and all residual solvent carried over from the chromatography process is removed using a rotary evaporator. In one or more embodiments, the purified cannabinoid may be resuspended in pentane one or more times during the evaporation process in order to wash the cannabinoid material to remove any other residual solvents. Properly executing these steps will produce a white, high purity (>99% by weight of a single cannabinoid) crystalline powder. Unlike previously disclosed methods, this high purity material is the starting point for the production of large, high-purity cannabinoid crystals.

The use of a high-purity crystalline starting material has important implications for the production of large crystal lattices. In essence, the technique disclosed herein removes the obligation of using extremes of temperature and pressure as well as the lengthy incubation times required to grow crystalline diamonds when starting from less pure starting materials. As such, it should be noted that this improvement over existing high-pressure growth chambers offers a safer alternative to the production of large cannabinoid crystal aggregates by removing the containment of volatile combustible solvents under pressure. This improvement has been recognized by local fire enforcement as a safe alternative to high pressure THCA diamond mining schemas by allowing for its use in highly populated urban centers. Thus, the disclosed use of pure cannabinoid feed stocks to generate supersaturated solutions that rapidly recrystallize under low pressure allows for the use of less hazardous conditions to grow cannabinoid crystals. Furthermore, the disclosed approach accelerates the crystallization process from days/weeks to hours.

In step 106, the high purity crystalline powder is dissolved in a solvent to create a solution. In some embodiments, the solvent used in this step 106 may be pentane. In other embodiments, the solvent may include any one or more of hexane, heptane, cyclohexane, petroleum ethers, dichloromethane, trichloromethane, tetrahydrofurane, diethyl ether, ethanol, methanol, isopropanol, acetone, acetonitrile and ethylacetate. In some embodiments, a ratio of mass of crystalline powder to volume of solvent is from 1:2 to 5:1, from 1:1 to 4:1, from 1:1 to 3:1, or about 3:1.

Next, in step 108, the solution is concentrated by removing solvent using heat and/or vacuum to generate a supersaturated solution. In some embodiments, step 108 consists of placing the solution in a appropriately rated fume hood designed for the purging of solvents. Depending on the solvent selected in step 106, the warming temperature and pressure may be selected to initiate evaporation of the solvent. For example, the warming temperature may be set at the boiling point of the solvent, or 10-40° C. below the boiling point of the solvent at the pressure used during the warming step 108. Solvents with higher boiling points will require either the use of a higher temperature and/or the application of deeper vacuum (lower pressure) to allow for the creation of a supersaturated solution via solvent evaporation. In some embodiments, step 108 is performed until 30-90 vol %, 40-80 vol %, or 50-75 vol % of the solvent has evaporated. In one or more embodiments, step 108 is performed on a pentane solution using an open, unpressurized vessel at ambient pressure or light vacuum at 70-90° C. and is completed when 50-75% of the pentane has been evaporated.

In step 110, a seed crystal is added to the supersaturated solution produced in step 108. The seed crystal may be supplied from an earlier iteration of the process 100, may be an original seed crystal formed from the high purity crystalline powder, or may be a commercially available seed crystal. In one or more embodiments, to produce an original seed crystal, the crystalline powder is heated to its "hard cracking" point using an oven, heating plate or external heat source, similar to working with sugar in candy making processes. For THCA crystalline powder, this process takes approximately 15-30 minutes at 165-195° F. Upon cooling at room temperature for 30-40 minutes or flash freezing at –20 Celsius for 15 minutes, small THCA crystal aggregates form. These aggregates may then be used as the starting seeds upon which larger THCA crystal lattices are built using a supersaturated solution as described herein. Similar processes may be applied for other cannabinoid crystalline powders. In some embodiments, a plurality of seed crystals may be added in step 110.

After step 110, the remaining solvent is evaporated in a step 112 as crystallization proceeds. During step 112, heat and/or vacuum are applied to maintain a supersaturated solution. That is, the seed crystal grows due to crystallization of the cannabinoid in the supersaturated solution, which reduces the concentration of the cannabinoid. As such, in order to maintain a supersaturated solution, the solvent must be removed (evaporated) to account for the loss of cannabinoid from the solution. The use of a high purity starting material, and the gradual evaporation of the solvent, leads to the formation of larger THCA crystals by maintaining a super saturated solution through the continual removal of solvent as crystallization occurs. The temperature and pressure conditions in step 112 may be the same as those described above for step 108. In some embodiments, the temperature may be higher and/or the pressure may be lower in step 112 as compared to step 108 because a larger seed crystal will result in faster crystallization thereby requiring more rapid evaporation to maintain a supersaturated solution. The rate of crystallization is directly proportional to the size of the seed crystal being used in the saturated solution. As such, larger crystal structures will increase in mass at a rate that is relative to their overall surface area. In one or more embodiments, growth of the crystal can exceed 1 gm/hour/crystal.

Next, in step 114, the crystal formations may be harvested after full evaporation of the solvent. In some embodiments, these crystal formations may be used as seed crystals in step 110 to grow larger and larger crystal structure. The limit of crystal structure is primarily dictated by the vessel size.

Example 1

High purity (>99% by weight) THCA crystalline powder was used as a starting material. A seed crystal was formed by heating a quantity of the THCA crystalline powder to its "hard cracking" point at 165-196° F. for 15-30 minutes. Upon cooling, small THCA crystal aggregates formed, which were used as seed crystals.

Next, 30 grams of THCA crystalline powder was dissolved in 10 ml of pentane to form a solution. The solution was warmed to 70-90° C. until 50-75 vol % of the pentane evaporated, thereby forming a supersaturated solution. A seed crystal produced above was then added to the supersaturated solution.

Figure 2:
FIG. 2 is a photograph of a THCA crystal produced according to an embodiment of the present disclosure.

The supersaturated solution and seed crystal were then warmed to 70-90° C. Crystallization occurred on the seed crystal and the solvent continued to be removed via evaporation. After the solvent was entirely evaporated, the crystal formations were removed from the vessel and used as seed crystals in a new supersaturated solution. After 12 hours of crystallization, a 7 gm THCA crystal was produced, which is shown in FIG. 2.

As described above, the present disclosure offers a safe and viable procedure, with unparalleled crystal growth per unit time, that mitigates the danger of conventional diamond mining rigs.

Although the present disclosure has been described using preferred embodiments and optional features, modification and variation of the embodiments herein disclosed can be foreseen by those skilled in the art, and such modifications and variations are considered to be within the scope of the present disclosure. It is also to be understood that the above description is intended to be illustrative and not restrictive. Many alternative embodiments will be apparent to those skilled in the art upon reviewing the above description. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the disclosure. Lastly, our description herein describes the method by which we obtain the highly purified starting material. It is conceivable that other methods, not simply just high-pressure liquid chromatography, can be implemented to obtain the starting crystalline feedstock used in part two of the example. In addition, there is more than one way to generate the starting growth seed in part one of the example. The focus of the present disclosure is how to grow large THCA crystals or "diamonds" by adding a refined, high purity TCHA feedstock to a recrystallization process that occurs at an accelerated rate through the maintenance of a supersaturated solution throughout crystal growth by the parallel removal of the carrier solvent through evaporation.

What is claimed is:

1. A method of forming a cannabinoid crystal, comprising:

(i) providing a powdered or crystalline cannabinoid isolate comprising 90 wt % or greater of a single cannabinoid;

(ii) dissolving the isolate in a crystallization solvent in which the cannabinoid is soluble to form a solution;

(iii) placing the solution under heat and/or vacuum until the solution reaches a saturation point to produce a saturated solution;

(iv) adding a seed crystal to the saturated solution; and (v) placing the resulting combination under heat and vacuum until the solvent is fully evaporated, thereby producing the cannabinoid crystal.

2. The method according to claim 1, further comprising repeating steps (i)-(v) using the cannabinoid crystal produced in step (v) as the seed crystal in step (iv).

3. The method according to claim 1, wherein the cannabinoid isolate is a THC, THCA, THCV, CBD, CBDA, CBDV, CBG or CBGA isolate.

4. The method according to claim 1, wherein the cannabinoid isolate is a THCA isolate.

5. The method of claim 1, wherein the crystallization solvent is pentane, hexane, heptane, cyclohexane, petroleum ethers, dichloromethane, trichloromethane, tetrahydrofurane, diethyl ether, ethanol, methanol, isopropanol, acetone, acetonitrile, ethylacetate, or combinations thereof.

6. The method according to claim 1, wherein the crystallization solvent is pentane.

7. The method according to claim 6, wherein step (iii) is performed at 70-90° C.

8. The method according to claim 1, wherein the cannabinoid isolate comprises 99 wt % or greater of a single cannabinoid.

9. The method according to claim 1, wherein in step (ii) a ratio of a weight of the cannabinoid isolate to a volume of the crystallization solvent is from 1:2 to 5:1.

10. The method of claim 1, wherein step (iii) is performed under a vacuum.

* * * * *